(12) United States Patent
Bangert et al.

(10) Patent No.: US 8,263,331 B2
(45) Date of Patent: Sep. 11, 2012

(54) DEVICE AND METHOD FOR THE DETECTION OF AN ANALYTE

(75) Inventors: Joachim Bangert, Erlangen (DE); Ludwig Bär, Erlangen (DE); Thomas Ehben, Weisendorf (DE); Hans-Dieter Feucht, Renningen (DE); Christian Zilch, Leipzig (DE)

(73) Assignee: Siemens Aktiengesellschaft, Munich (DE)

( * ) Notice: Subject to any disclaimer, the term of this patent is extended or adjusted under 35 U.S.C. 154(b) by 506 days.

(21) Appl. No.: 11/655,943

(22) Filed: Jan. 22, 2007

(65) Prior Publication Data
US 2007/0190640 A1    Aug. 16, 2007

(30) Foreign Application Priority Data
Jan. 23, 2006 (DE) .......................... 10 2006 003 177

(51) Int. Cl.
*C12Q 1/68*    (2006.01)
*C12M 1/00*    (2006.01)

(52) U.S. Cl. ..................................... 435/6.1; 435/283.1

(58) Field of Classification Search ............... 435/283.1, 435/6.1
See application file for complete search history.

(56) References Cited

U.S. PATENT DOCUMENTS

| | | |
|---|---|---|
| 6,485,985 B1 | 11/2002 | Weitschies et al. |
| 2003/0006143 A1 | 1/2003 | Banerjee et al. |
| 2004/0106009 A1 * | 6/2004 | Nakamura et al. .......... 428/694 R |
| 2005/0087000 A1 | 4/2005 | Coehoorn et al. |
| 2005/0112655 A1 * | 5/2005 | Banerjee et al. .................. 435/6 |
| 2005/0148100 A1 | 7/2005 | Su et al. |
| 2005/0245658 A1 * | 11/2005 | Mehrotra et al. ............. 524/430 |

FOREIGN PATENT DOCUMENTS

| | | |
|---|---|---|
| DE | 195 03 664 A1 | 8/1996 |
| WO | WO 03/019186 A1 | 3/2003 |
| WO | WO 03/043931 A1 | 5/2003 |
| WO | WO-2005/111596 A1 | 11/2005 |
| WO | WO 2006/061835 * | 6/2006 |
| WO | WO 2006/104700 A1 | 10/2006 |

OTHER PUBLICATIONS

Barnakov et al., Langmuir., vol. 21, pp. 7524-7527, available on the Web Jun. 30, 2005.*
Staroduobtsev et al. Microelectronic Engineering, vol. 69, pp. 324-329, 2003.*
M.Albrecht et al.: "Magnetic multilayers on nanospheres", nature materials, www.nature.com/naturematerials, 2005, published online: Feb. 13, 2005, pp. 1-4.
European Search Report.
Chemla, Y.R. [u.a.]: Ultrasensitive magnetic biosensor for homogeneous immunoassay, Proceedings of the National Academy of Science of the USA (2000), vol. 97, Nr. 26, S. 14268-14272.
German Office Action.

* cited by examiner

*Primary Examiner* — Gary Benzion
*Assistant Examiner* — Cynthia Wilder
(74) *Attorney, Agent, or Firm* — Harness, Dickey & Pierce, P.L.C.

(57) ABSTRACT

A device and a method are disclosed for the detection and/or for the quantification of an analyte. In at least one embodiment, the device includes a basic matrix and magnetized nanoparticles, which are arranged in moveable fashion in or at the basic matrix and to which catcher molecules that bind specifically to the analyte are anchored. Further, the mobility of the nanoparticle in the basic matrix can be influenced by a binding of the analyte to be detected to the catcher molecules and can be read out magnetically.

20 Claims, 4 Drawing Sheets

DEVICE AND METHOD FOR THE DETECTION OF AN ANALYTE

PRIORITY STATEMENT

The present application hereby claims priority under 35 U.S.C. §119 on German patent application number DE 10 2006 003 177.6 filed Jan. 23, 2006, the entire contents of which is hereby incorporated herein by reference.

FIELD

Embodiments of the invention generally relate to a device and/or a method for the detection and/or for the quantification of an analyte with the aid of catcher molecules that bind specifically to the analyte.

BACKGROUND

Devices and methods are used in the prior art, in particular for the detection of biomolecules such as nucleic acids or proteins. In the case of protein assays, the proteins couple e.g. to specific monoclonal antibodies, while DNA or RNA strands are detected by using respectively complementary nucleic acids as catcher molecules.

Most nucleic acid and protein detection methods by use of biosensors require a marking of the biomolecules to be examined. The molecular markers used for this purpose may be fluorescent, luminescent or electrically or magnetically active molecules or particles (quantum dots, magnetic beads). After a hybridization e.g. with complementary DNA catcher molecules in a homogeneous phase or at a microarray, the markers are detected at the bound biomolecules by means of optical, electrical or magnetic measuring methods.

One exception is the gravimetric method, which, with the aid of piezosensors, detects the change in mass through addition of molecules to the sensor surface. The nucleic acids or proteins do not need to be marked in this case. What prove to be disadvantageous, however, are the relatively low sensitivity, the small dynamic measurement range and the relatively complicated production methods for producing the piezooscillators under the sensor layers.

In the case of the known array-based detection methods, before the hybridization or binding of the analyte to the catcher molecules, markers are bound to the sample molecules (analyte) to be detected. The markers are detected after a hybridization or binding that has taken place. For this purpose, the microarray is introduced into an evaluation unit that detects the optical, electrical or magnetic marker signals. For this purpose, the evaluation unit contains a sensor array, which measures the signal emission of each individual array dot in parallel or sequentially. This gives rise to stringent requirements made of integration and homogeneity of the sensor array.

SUMMARY

In at least one embodiment of the invention, an improved device and/or a corresponding method is provided for the detection and/or for the quantification of an analyte with the aid of catcher molecules which do not have at least one of the disadvantages presented above, in particular do not require prior marking of the analyte to be detected.

In at least one embodiment, the invention proposes a device having a basic matrix and at least one magnetized nanoparticle which is arranged in moveable fashion in or at the basic matrix and to which catcher molecules that bind specifically to the analyte are anchored, wherein the mobility of the nanoparticle in the basic matrix can be influenced by a binding of the analyte to be detected to the catcher molecules and the changed mobility of the nanoparticle can be read out magnetically. The term "bind" is intended to mean not only a covalent binding, but e.g. also a hybridization.

The basic matrix is preferably a gel matrix. A crosslinked gel matrix may be based for example on polyacrylamide, polyacrylic acid, polyhydroxyethyl methacrylate, polyvinyl alcohol or polyvinyl pyrrolidone or copolymers which contain corresponding monomer sequences. The gel matrix may be crosslinked for example thermally or by UV light before or after the nanoparticles have been introduced. As an alternative, however, the basic matrix may also be formed by any other colloid, a fluid or a pulverulent material.

The nanoparticles, also called "beads" hereinafter, preferably have an at least approximately spherical or elliptical form and a diameter of approximately 10 nm-10 μm, in particular 20 nm-1 μm, and particularly preferably approximately 50-500 nm. They may be produced e.g. in accordance with the method described in the article by Albrecht M. et al. "Magnetic multilayers on nanospheres", nature materials, 2005, pages 1-4 (the entire contents of which is hereby incorporated herein by reference), that is to say a core made of polystyrene and a magnetic coating, in particular made of CoPb.

The beads are preferably constructed differently, however; by way of example, in accordance with a particularly preferred embodiment, they include a ball of polystyrene that is permeated with magnetic particles. The basic material polystyrene enables good binding of the catcher molecules to the surface. The magnetic particles preferably have an elongate, in particular acicular, form, with the result that they cannot rotate within the polystyrene and, consequently, the magnetization direction of the bead is defined.

As an alternative, the beads may be constructed in solid fashion from a magnetic material. The magnetic material of the beads or of the magnetic particles contained therein may be for example CoPb, CoPt, $CrO_2$, CrFe, Ni compounds or NdFeB.

The beads should have only one magnetization, in particular a dipole magnetization. The beads preferably have anisotropic, hysteretic properties, that is to say that they maintain their magnetization axis with respect to their polar axis over a defined magnetic field strength range. The hysteresis of their magnetic characteristic has the effect that the nanoparticles are not subjected to magnetization reversal during the writing operations described below, but rather only change their spatial orientation, for instance like a compass needle. The bead is constituted such that an anisotropy axis provides for a fixed orientation of the magnetic polarization relative to the bead geometry.

Preferably, the beads are arranged in one or more layers near or at the gel matrix surface.

The catcher molecules may be anchored to the nanoparticles in any desired manner; in particular, they may be applied to the surface of the nanoparticles as a coating. If appropriate, they may also be bonded to the nanoparticles by means of linker molecules.

Preferably, a number of adjacent beads are in each case combined to form a group, referred to as "spot" hereinafter. These are preferably in each case equipped with identical catcher molecules. In the extreme case, however, a spot may also comprise a single bead. Preferably, a large number of spots are arranged on a basic matrix in the form of a matrix or an "array", e.g. in a 5×5 to 50×50 array. The "pitch", that is to say the distance between the centers of the spots, is e.g. 1-500

μm, preferably 10-100 μm. The diameter of an individual spot is e.g. 0.5 to 1 pitch. Given a diameter of 1 pitch, adjacent spots touch one another, which is possible in principle. The basic area of the individual spots is e.g. circular or rectangular with rounded corners.

The crosslinking of the gel matrix is preferably configured by controlling the crosslinking density in such a way that the magnetic beads are on the one hand permanently enclosed in the basic matrix, but on the other hand can still be wholly or partly rotated, whereby the anisotropy axis of the bead magnetic field (position of magnetic north pole and south pole) is changed as well. If all the beads of a spot have the same magnetic orientation, a magnetic field whose orientation corresponds to that of the individual beads emanates from the spot. With a magnetic field sensor it is possible to detect said orientation metrologically. If the sensor is embodied as a write-read head in a manner similar to that in the case of a conventional storage hard disk, in addition the magnetic field orientation of a spot can thereby be changed. In the case of such reversal of the magnetization of a spot, all the beads associated with the spot are rotated.

Preferably, the analyte to be detected is a biomolecule, e.g. a nucleic acid or a protein and the catcher molecules are nucleic acids or monoclonal antibodies, the analyte binding to the catcher molecules by hybridization or antigen-antibody reaction.

In order to detect biomolecules in a sample using an array of such beads in a gel, said biomolecules to be detected are preferably isolated from the sample in one or more processing steps and are subsequently applied to the gel. They pass to the surface of the beads. This may take place either as a result of diffusion through the gel or by virtue of the fact that the beads are arranged at the gel surface and as a result partly project from it. The presence or absence of biomolecules then changes the mechanical and hence the magnetic properties of the array. This can happen in three different ways:

In accordance with the first variant, the target molecules bind specifically to catcher molecules on the bead. Solely as a result of this, the rotatability of the beads in the gel matrix is wholly or partly prevented, in particular for the case where large molecules, e.g. long molecular chains such as long DNA or RNA strands or amino acid chains, or sterically bulky molecules are involved. The rotatability of the beads is reduced e.g. by the molecular entwining of the target molecules with the surrounding matrix. The hybridization or binding to the bead surface may also take place outside the matrix at the interface thereof. A diffusion of the target molecules into the matrix is not necessary in this case. The degree of limitation of the rotatability is determined in this case by the number of catcher/target molecule complexes per bead. For this detection variant it suffices for the catcher molecules to address, if appropriate, only a specific sequence of the DNA or RNA strands to be detected.

In accordance with a second variant, the beads of a spot are in each case coated such that the target molecules can form molecular bridges between the beads. Preferably, for this purpose the beads in a spot are equipped with at least two different catcher molecules that are specific to different regions of the target molecule to be detected. By way of example, for this purpose specific target sequences are selected at the beginning and end of a molecule sought. The molecular bridges between the beads result in a significant limitation of the mobility of the magnetic beads, as a result of which they are prevented from a free rotation or rotate back into their starting position again after a small rotation as a result of an external magnetic field.

The presence of molecules to be detected can therefore be detected by the fact that the beads are not aligned in a magnetic field. In other words, it is not possible to detect a "magnetization" of a spot in a subsequent measurement. The spot therefore behaves like a writable bit of a hard disk without hybridization or binding and like a non-writable bit with hybridization or binding. In the case of this variant, the use of multiple layers ("multilayers") is particularly expedient since a large number of beads thereby contribute to the generation of the total magnetic field of a spot.

As an alternative or in addition, molecular networks may be established between the magnetic beads of a spot using a chemical crosslinker. In this case, the catcher molecules of the magnetic beads only have to bind specifically to a region of the target molecules. In order to ensure a subsequent crosslinking, the target molecules are terminally marked with a chemical group which undergoes a crosslinking with chemical groups of identical type under specific chemical or physical conditions. If this label is e.g. an aminoalkyl group, then the crosslinking may be effected by addition of $\alpha$, $\omega$-dicarboxylic acids such as e.g. $\alpha$, $\omega$-polyethylene glycol dicarboxylic acid.

In accordance with a third variant, catcher molecules specific to the target molecules are anchored not only on the beads but also in the basic matrix or at the interface thereof. In the case of a hybridization or binding, bridges form between these anchored catchers and those on the bead surface, which partly or wholly prevent a rotation of the bead. In this case, the catchers on the bead are specific to a first region and those anchored on or in the matrix are specific to a second region of the target molecules. The binding events are detected as in the case of the second variant. This in turn also applies to the use of chemical crosslinking. The addressing of only a specific target sequence by the catcher suffices here, it being necessary for the target molecules to carry a label capable of crosslinking.

In addition to the catcher molecules, the beads and, in the case of the third variant, also the basic matrix can be provided with streptavidin molecules. In this case, the target molecules are bonded to a biotin molecule in a region at the start and, in the case of the second and third variants, also at the end of the target molecular chain. In the case of a binding, the target molecules in this way form very stable molecular bridges to a bead, between the beads or between a bead and the basic matrix by virtue of adhering to the beads both via their biotin complex and via the catcher molecules (e.g. with their specific sequence).

The method described, in at least one embodiment, allows a particularly high sensitivity to be expected since even a small number of molecular bridges should lead to prevention of the rotatability of the beads. An amplification of the target molecules to be detected in the case of nucleic acid assays can therefore preferably be dispensed with, although in the case of genomic DNA a fragmentation of the DNA is often expedient. The construction of the measuring device is therefore greatly simplified by the omission of numerous microfluidic components. Moreover, the restriction to a small number of molecule types to be detected that is customary in amplifications (e.g. multiplex PCR: typically<10 multiplex channels) is obviated.

In order to obtain, on the one hand, ready diffusion of the target molecules to the beads and, on the other hand, in the case of a binding to be detected, high holding forces of the target molecule/catcher complexes, the degree of crosslinking of the matrix is increased after the hybridization by a post-crosslinking in one example embodiment. The post-crosslinking may also lead to a binding of target molecule/ catcher complexes with the matrix over and above the entwining. The molecular holding forces that can be obtained are particularly high in this case. The post-crosslinking may be effected e.g. by irradiation with UV light, by heat or by addition of suitable chemicals.

At least one embodiment of the invention is also directed at a corresponding method for the detection and/or for the quantification of an analyte, in which the changed mobility of a nanoparticle in a basic matrix is read out magnetically. Example writing and reading operations are explained in more detail below.

BRIEF DESCRIPTION OF THE DRAWINGS

The invention will now be described in more detail on the basis of example embodiments with reference to the accompanying drawings, in which.

DETAILED DESCRIPTION OF THE EXAMPLE EMBODIMENTS

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

Figure 1:
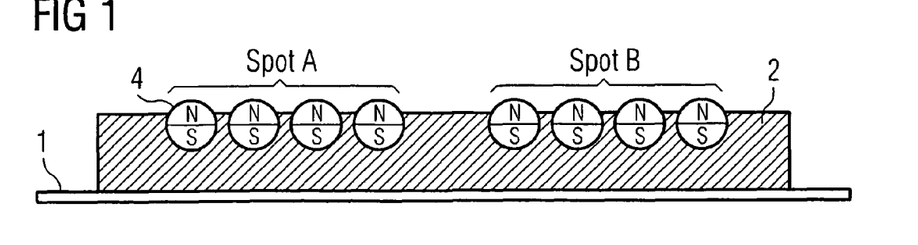
FIG. 1 shows a schematic cross section through a measuring device in accordance with a first embodiment of the invention.

FIG. 1 schematically shows a measuring device in accordance with a first embodiment of the invention. In this case, spherical, magnetic nanoparticles or beads 4 are embedded into a gel matrix 2 at the surface thereof, so that they are approximately half covered by the gel. As an alternative, they may also lie on the surface of the gel.

The gel matrix is arranged on a carrier or a baseplate 1 made of any desired material. As can be seen from FIG. 1, the beads 4 are grouped to form two spots A and B each having four beads. In practice, each spot generally comprises approximately 10-10 million, preferably approximately 1000-1 million, nanoparticles. These are then embedded into the basic matrix in multiple layers, or in random, amorphous arrangement.

Figure 2:
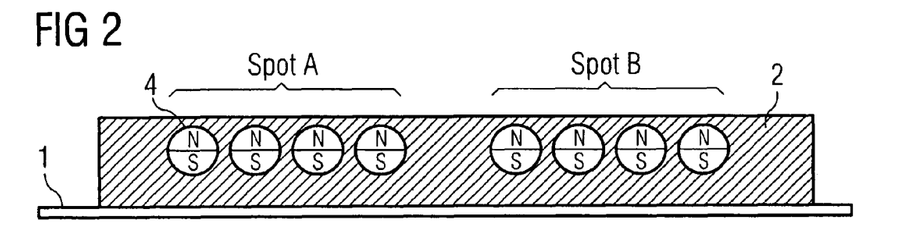
FIG. 2 shows a schematic cross section through a measuring device in accordance with a second embodiment of the invention.

In the embodiment of FIG. 2, by contrast, the beads 4 are completely embedded into the gel matrix 2. The catcher molecules anchored on the surface of the beads are not illustrated in FIGS. 1 to 6.

Figure 3:
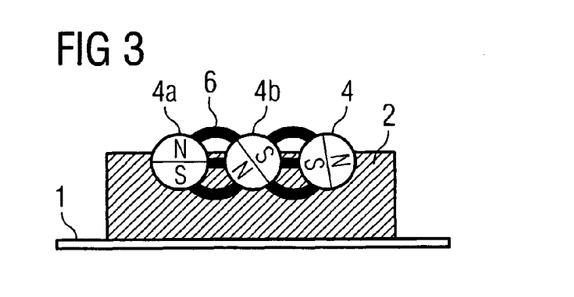
FIG. 3 shows an enlarged excerpt from the illustration of FIG. 1, with target molecules bound to the beads in accordance with the second variant.

FIG. 3 shows the effect of the attachment of target molecules or analyte 6 to the nanoparticles 4, to be precise in the case of a configuration of the measuring device in accordance with the second variant described above. In this case, the beads 4 in a spot are equipped with two different catcher molecules that bind to different regions—which are preferably far away from one another—of the target molecules. As a result, by way of example, the start of a DNA strand sought hybridizes to a first bead 4a and the end of the strand hybridizes to an adjacent bead 4b, for the formation of a molecular bridge 6. The bead 4b is immobilized by e.g. 6 molecular bridges of this type to e.g. two adjacent beads 4a and 4 and can no longer be rotated.

In this example embodiment, either each bead in a spot may be coated with two different catcher molecules, or the spot contains a mixture of two different types of beads each having a different catcher molecule.

Figure 4:
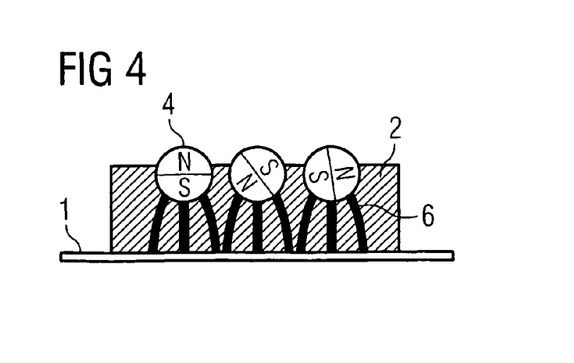
FIG. 4 shows an enlarged excerpt from the illustration of FIG. 1, with target molecules bound to the beads in accordance with a first embodiment of a third variant.
Figure 5:
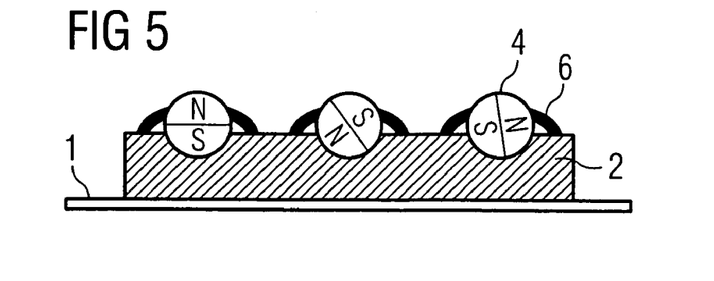
FIG. 5 shows an enlarged excerpt from the illustration of FIG. 1, with target molecules bound to the beads in accordance with a second embodiment of a third variant.

FIGS. 4 and 5 show an example embodiment in accordance with a third variant, in which catcher molecules are likewise anchored to the basic matrix 2. Said catcher molecules, as illustrated in FIG. 4, may be anchored to the baseplate or the carrier 1 or, as illustrated in FIG. 5, may be anchored directly in the basic matrix 2 or at the interface thereof with the surroundings. Molecular bridges 6 between the beads 4 and the basic matrix 2 are formed here as a result of the attachment of target molecules to the catcher molecules, as a result of which bridges the beads 4 are restricted in their mobility and in particular rotatability.

Figure 6:
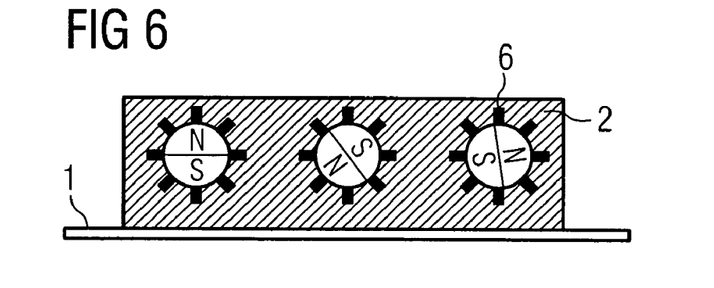
FIG. 6 shows an enlarged excerpt from the illustration of FIG. 2, with target molecules bound to the beads in accordance with the first or third variant.

FIG. 6 shows an example embodiment in accordance with the first variant described above, in which the mobility, in particular rotatability, of the beads 4 is reduced simply by the binding of the target molecules 6 to said beads. This variant is recommended particularly in the case of large and/or sterically bulky target molecules 6 which cannot be moved without resistance from the beads 4 through the basic matrix 2. In addition, the target molecules 6, in accordance with the third variant, can be anchored in the basic matrix at their other end.

Figure 7:
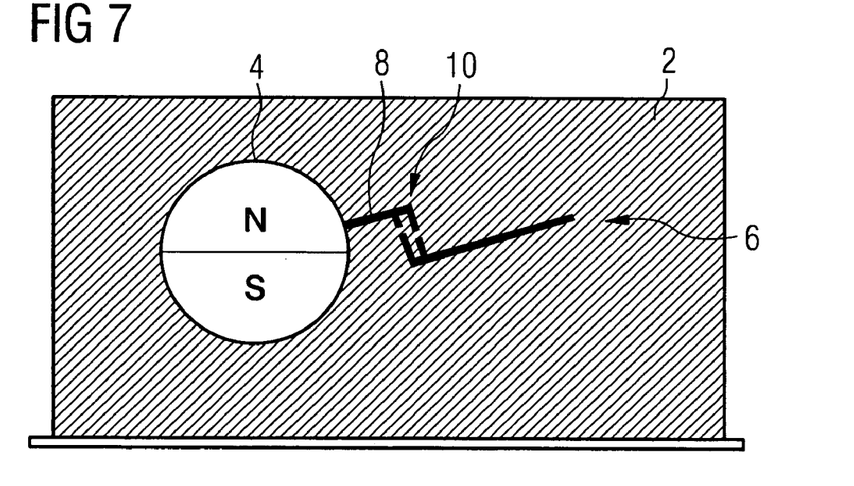
FIG. 7 shows an enlarged illustration of a nanoparticle in accordance with FIG. 6 with a hybridized or crosslinked catcher molecule.

FIG. 7 shows a nanoparticle 4 in the gel bed 2 in an enlarged cross-section. The nanoparticle acts like a bar-type permanent magnet and therefore has a north pole N and a south pole S. A linker 8 is anchored to the surface of the nanoparticle 4, the catcher molecule 10 in turn being attached to said linker. The catcher molecule 10 has a section that is complementary to a section of a target molecule 6 and therefore binds to the latter.

The detection method with the aid of a magnetic read-out will now be explained with reference to FIGS. 8 to 10 and 11 to 13.

Figure 8:
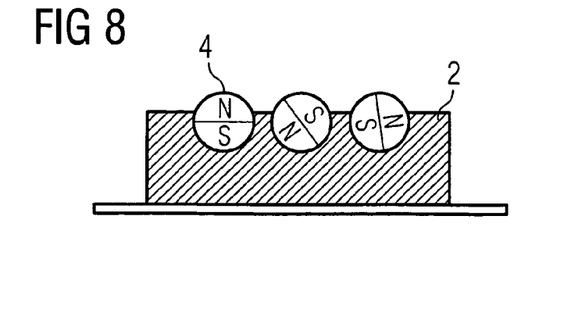
FIG. 8 shows a cross section through a spot composed of nanoparticles to which no target molecules are bound, in the initial state.
Figure 9:
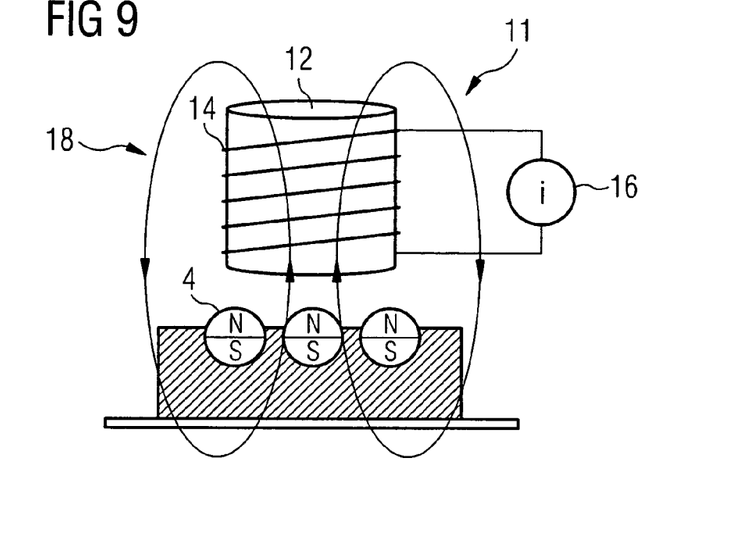
FIG. 9 shows a cross section through the spot from FIG. 8 and a write-read head during the writing operation.
Figure 10:
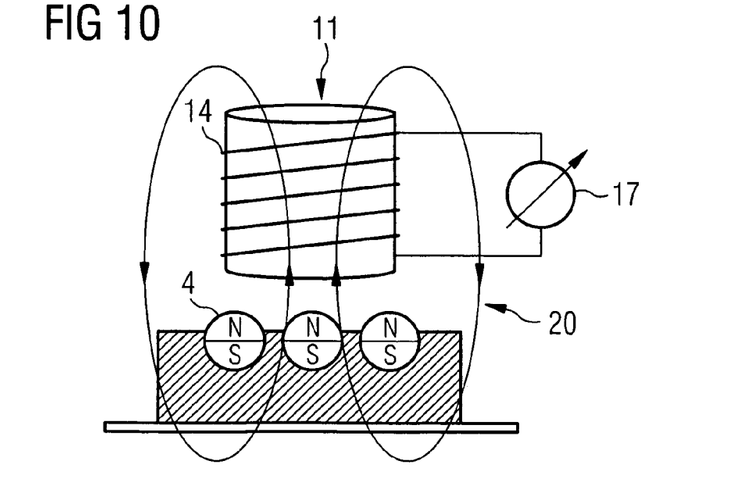
FIG. 10 shows a cross section through the spot from FIG. 8 and a write-read head during the read-out operation.

FIGS. 8-10 illustrate a measuring operation in the case of a spot composed of beads 4 to which no target molecules are bound. FIG. 8 shows the spot in the initial state. FIG. 9 illustrates the writing operation. In this case, a magnetic field 18 is generated in the basic matrix by way of a write-read head 11. Said magnetic field has the effect that all the beads 4 of a spot are aligned in the same direction, to be precise by a rotation about their own axis. The north poles N of the beads 4 therefore all point upward in FIG. 9.

The write-read head 11 contains a coil 14 having a winding and a coil core 12, which coil acts as an electromagnet during the writing operation. The coil 14 is connected to a current source 16 for generating a magnetic field 18 of defined strength that is as homogeneous as possible over the spot.

The magnetic field 20 generated by the aligned beads 4 is detected by the write-read head 11 during read-out in accordance with FIG. 10. In the case illustrated, the beads 4 of a spot are all aligned in one direction with their north and south poles, with the result that a magnetic field 20 is read out. This indicates that no target molecule has been bound and, as a result, all the beads of the spot are freely rotatable. The test therefore proved negative.

The reading or writing operation can take place in different ways:

Firstly, a static magnetic field can be applied during writing and the static magnetic field generated by the beads 4 can be measured during read-out, e.g. by means of a Hall sensor or magnetoresistive sensor, e.g. a GMR, TMR, AMR or CMR sensor, (not illustrated) contained in the write-read head 11.

Secondly, the write-read head can move over the spots along the array during read-out, so that a voltage is induced in the coil 14 in each case when there is a change in the magnetic field from one spot to the next. Said voltage is measured by a voltmeter 17 of the write-read head 11. This procedure corresponds to the principle of read-out from magnetic data storage media.

In the first and second methods, it is advantageous to magnetize each spot firstly in a direction ("0"), to read out the magnetic field generated by the spot, and then to magnetize the spot in the opposite direction ("1") and to read out the magnetic field once again. This is important for the case where the beads were randomly identically aligned prior to the binding with the target molecules, so that the spot exhibits a magnetization e.g. in the direction "0". This would lead to the conclusion in a single write-read operation that the beads were aligned as a result of the writing operation and are therefore unbound, even though they are actually immobilized by the binding with target molecules.

Thirdly, a dynamic type of writing and reading is also possible. In this case, the coil 14 is excited e.g. by an alternating current, with the result that it generates a periodically oscillating magnetic field. The magnetic beads 4 therefore start to rotate periodically with the alternating magnetic field. Due to their inertia, this "oscillation" is slightly delayed relative to the oscillation of the magnetic field. When the oscillating magnetic field is turned off, the beads likewise affect a degree of post-oscillation on account of their inertia. This delay or the post-oscillation can be detected on the basis of the voltage induced in the coil 14. If the beads 4 are bound to target molecules 6, however, they do not concomitantly rotate or oscillate, which can likewise be detected.

In all of the writing and reading methods, the write-read head 11, for writing to and reading from an array of spots in a measuring device, is moved relative to the basic matrix 2, in particular along the gel surface. For this purpose, the head 11 can be moved relative to the array in the measuring device, or the measuring device can be moved relative to the head. Both can take place in the form of a translational movement (array of columns and rows) or a rotational movement (circular or spiral form of the array).

Figure 11:
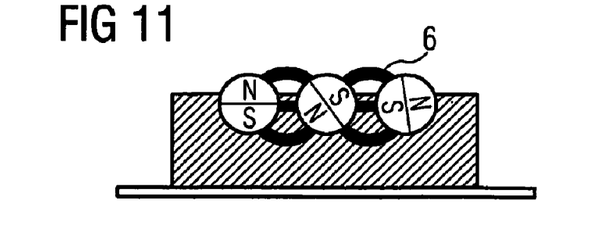
FIG. 11 shows a cross section through a spot composed of nanoparticles to which target molecules are bound, in the initial state.
Figure 12:
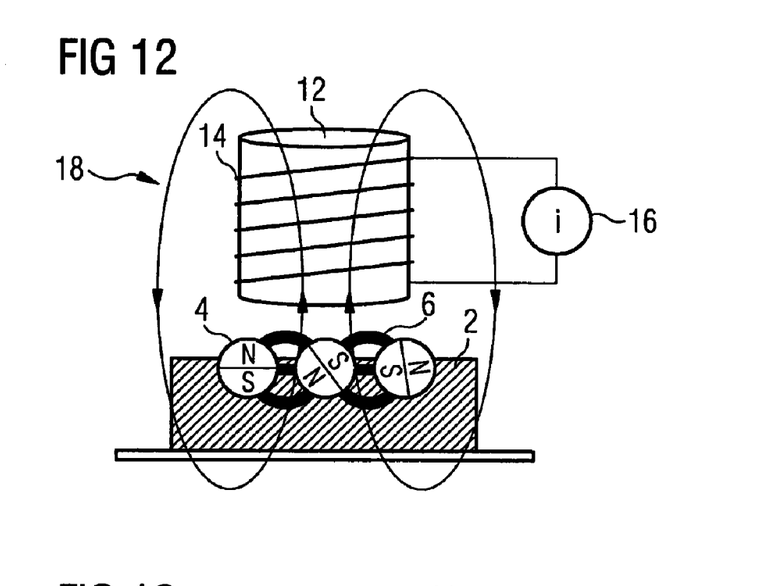
FIG. 12 shows a cross section through the spot from FIG. 11 and a write-read head during the writing operation.
Figure 13:
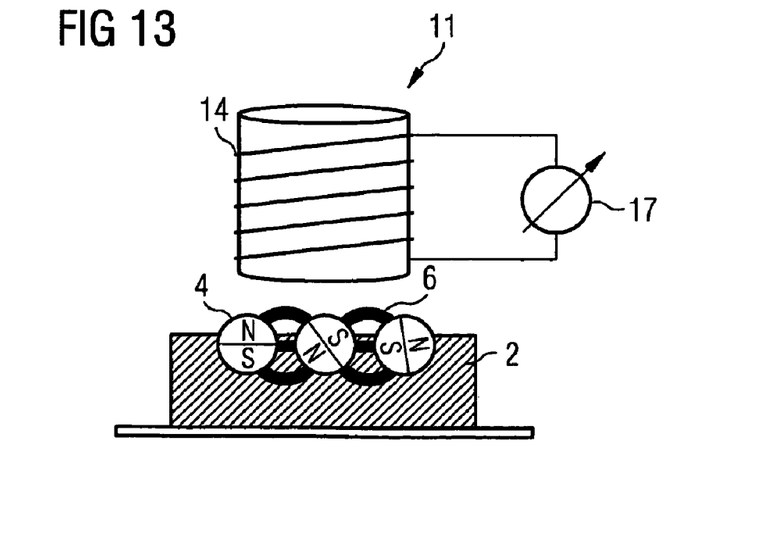
FIG. 13 shows a cross section through the spot from FIG. 11 and a write-read head during the read-out operation.

FIGS. 11 to 13 illustrate a writing and reading operation in which the presence of target molecules is detected by virtue of the fact that molecular bridges 6 have been formed between the beads 4 of the spot. The writing operation illustrated in FIG. 12 is not successful, therefore; the beads 4 remain in their initial position. As a result, no magnetization is achieved by the write-read head 11 in the spot during the writing operation. The magnetic dipoles of the beads 4 are not aligned together and therefore do not generate a magnetic field toward the outside. Therefore, no voltage is induced in the volt meter 17 in the reading operation illustrated in FIG. 13.

A quantitative measurement can be effected by way of the method described because the tearing-loose moment per bead, that is to say that torque that has to be overcome in order to rotate a bead with the molecular bridges being torn apart or with the entwining with the basic matrix molecules being released, depends on the number of molecular bridges per bead and hence on the concentration of the target molecules to be detected. The tearing-loose moment can be determined by performing writing operations with a rising magnetic field strength in an attempt to rotate the magnetization axis of the spots. The success of the respective attempts can be verified by reading operations. Starting from a specific magnetic field strength, the beads tear loose or break away and retain the magnetization direction impressed during the respective writing operations.

As an alternative, a quantitative measurement is possible in that the number of beads fixed by molecular bridges per spot depends on the concentration of the sample molecule to be detected in each case and influences the degree of magnetization 20 that remains after the writing operation (magnetization remanence).

The method furthermore permits a calibration of the measuring device for optimization of the accuracy primarily in quantitative measurements. The spot-to-spot variants of the chemical, mechanical and/or magnetic properties can occur during the production of the array, which restrict the meaningfulness of quantitative measurements. By way of example, the gel is of varying viscosity at different locations, with the result that the nanoparticles in different spots have a varying rotatability, which in turn influences the magnetization reversibility of each spot. In order to combat this effect, the degree of magnetization reversibility of each spot is preferably detected by way of an above-described write-read operation as early as before the sample extract containing the target molecules is added. The measurement results detected after the binding of the target molecules can then be corrected with the measurement results obtained previously.

In conventional microarrays, a variation of the hybridization temperature is often used for SNP or mutation analyses in order to check the binding strength of the molecular bridges (temperature stringency, melting curve). This procedure is likewise possible with the arrangement described here. For this purpose, the temperature of the gel and of the beads can be varied e.g. during the hybridization and/or the read-out.

In a further embodiment, the beads of the array are pre-magnetized as early as during production, that is to say prior to the hybridization with a target molecule. This can be done in a manner such that different magnetization directions are impressed on spots or partial regions of spots, that is to say e.g. the magnetization direction with a north pole pointing upward as illustrated in the figures, or a different magnetization direction in which the north pole points toward the side, etc. The patterns of the magnetization directions may carry digital information which can be read out again after the hybridization operation if a hybridization actually took place at the respective spot or partial region of the spot (in the case of proteins the same holds true analogously for binding events). Suitable information that can be stored in this way includes e.g.: coordinate information; this may be expedient if very simple, e.g. manual, propulsion mechanisms are used for the write-read head, or direct statements about molecular-biological insights accompanying a hybridization event.

The embodiments described have the advantage, inter alia, that it is possible to adopt technology components from conventional hard disks, thus e.g. the movement components of the rotary disk and of the write-read head and also the electromagnetic function thereof. The use of novel magnetic storage materials and components from conventional data storage technology permits extremely high information densities that surpass microarray systems in use at the present time. Furthermore, known colloids and gels and known magnetic particles may be used as the basic matrix. Owing to the sensitivity that is to be expected, an amplification of the target molecules can be dispensed with for many applications.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A device for at least one of the detection and quantification of an analyte with the aid of a plurality of catcher molecules that bind specifically to the analyte, the device comprising:
   a basic matrix; and
   a plurality of magnetized nanoparticles arranged in a moveable fashion and in at least one layer within in the basic matrix, the catcher molecules that bind specifically to the analyte being anchored to the magnetized nanoparticles,
   wherein mobility of the magnetized nanoparticles in the basic matrix is influenceable by a binding of the analyte to be detected to the catcher molecules, a change in the mobility of the magnetized nanoparticles being magnetically readable,
   wherein, the plurality of magnetized nanoparticles are spatially combined to form a spot that is provided with at least two different types of the catcher molecules, different molecular regions of the analyte being crosslinked to different types of the catcher molecules,
   wherein the magnetized nanoparticles have an ellipsoidal form, and
   wherein the basic matrix is a gel matrix with a crosslinking density, each of the magnetized nanoparticles being permanently enclosed within said gel matrix such that each of the magnetized nanoparticles can be wholly or partially rotated.

2. The device as claimed in claim 1, wherein each of the magnetized nanoparticles has an approximately spherical form.

3. The device as claimed in claim 1, wherein each of the magnetized nanoparticles includes a basic body made of plastic that is permeated with a plurality of magnetic particles.

4. The device as claimed in claim 1, wherein each of the nanoparticles has a diameter of approximately 10 nm-10 μm.

5. The device as claimed in claim 1, wherein each of the nanoparticles includes an anisotropic magnetization and hysteresis properties.

6. The device as claimed in claim 1, wherein the analyte to be detected is at least one of a nucleic acid and a protein,
   the catcher molecules are at least one of nucleic acids and monoclonal antibodies, and
   the analyte binds to the catcher molecules by at least one of hybridization and an antigen-antibody reaction.

7. The device as claimed in claim 1, wherein, the plurality of nanoparticles are in the basic matrix.

8. The device as claimed in claim 7, wherein a plurality of the spots are in the basic matrix, each of the spots being provided with different types of the catcher molecules.

9. The device as claimed in claim 1, wherein rotatability of the nanoparticles is reducible by binding of the analyte to the catcher molecules.

10. The device as claimed in claim 1, wherein the catcher molecules are anchored in at least one of the basic matrix and at an interface of the basic matrix.

11. The device as claimed in claim 1, wherein the analyte is labeled with a chemical group which undergoes a crosslinking with chemical groups of an identical type under specific chemical or physical conditions.

12. The device as claimed in claim 1, further comprising a write-read head configured to measure a spatial orientation of at least one of the nanoparticles and the spot of the nanoparticles by detecting a magnetic field generated by the nanoparticles or the spot of nanoparticles.

13. The device as claimed in claim 12, wherein the write-read head is configured to change the spatial orientation of the nanoparticles or the spot of nanoparticles by application of a specific magnetic field if the mobility of the nanoparticles is not influenced by the binding of the analyte to be detected to the catcher molecules of the nanoparticles or the spot of nanoparticles.

14. The device as claimed in claim 3, wherein the plastic is polystyrene.

15. The device as claimed in claim 1, wherein each of the nanoparticles has a diameter of approximately 20 nm-1 μm.

16. The device as claimed in claim 1, wherein each of the nanoparticles has a diameter of approximately 50-500 nm.

17. The device as claimed in claim 1, wherein the different molecular regions of the analyte respectively correspond to a region at the start and a region at the end of a molecular chain of the analyte.

18. The device as claimed in claim 10, wherein the different molecular regions of the analyte include a region at the start and a region at the end of a molecular chain of the analyte.

19. The device as claimed in claim 1, wherein, the plurality of magnetized nanoparticles are arranged at the basic matrix.

20. The device as claimed in claim 19, wherein a plurality of the spots are at the basic matrix, the spots in each case being provided with different types of the catcher molecules.

* * * * *